United States Patent
Durand et al.

(10) Patent No.: US 6,587,725 B1
(45) Date of Patent: Jul. 1, 2003

(54) METHOD AND APPARATUS FOR CLOSED-LOOP STIMULATION OF THE HYPOGLOSSAL NERVE IN HUMAN PATIENTS TO TREAT OBSTRUCTIVE SLEEP APNEA

(76) Inventors: Dominique Durand, 36765 Valley Forge Dr., Solon, OH (US) 44122; Mesut Sahin, 711 S. Vienna, Ruston, LA (US) 71270; Musa A. Haxhiu, 3683 Meadowbrook Blvd., University Heights, OH (US) 44118

( * ) Notice: Subject to any disclaimer, the term of this patent is extended or adjusted under 35 U.S.C. 154(b) by 0 days.

(21) Appl. No.: 09/744,640
(22) PCT Filed: Jul. 27, 1999
(86) PCT No.: PCT/US99/16913
§ 371 (c)(1), (2), (4) Date: Mar. 26, 2001
(87) PCT Pub. No.: WO00/06249
PCT Pub. Date: Feb. 10, 2000

Related U.S. Application Data
(60) Provisional application No. 60/094,263, filed on Jul. 27, 1998.

(51) Int. Cl.[7] .................................................. A61N 1/18
(52) U.S. Cl. ........................................ 607/42; 607/118
(58) Field of Search ............................. 607/1, 2, 42, 48, 607/58, 62, 63, 116, 118, 134, 148; 128/848; 600/529, 538, 590, 26

(56) References Cited

U.S. PATENT DOCUMENTS
| | | | |
|---|---|---|---|
| 4,830,008 A | | 5/1989 | Meer |
| 5,540,732 A | * | 7/1996 | Testerman .................... 607/42 |

* cited by examiner

Primary Examiner—George R. Evanisko
(74) Attorney, Agent, or Firm—Fay, Sharpe, Fagan, Minnich & McKee, LLP (57) ABSTRACT

This invention is a fully implanted functional electrical stimulator (20) apparatus, a method for treatment of obstructive sleep apnea that provides for both reliable detection/prediction or airway occlusion that relieves, and/or prevents same by selective, direct electrical stimulation of the hypoglossal nerve (HG). The method, and apparatus sense hypoglossal nerve electro-neurogram activity for purposes of detecting or predicting obstructive sleep apnea. The sensed hypoglossal nerve activity, itself, is used to trigger functional electrical stimulation of the hypoglossal nerve in order to improve upper airway patency. Further, an improved hypoglossal nerve stimulation electrode (10) interface (IC) is provided that allows for simultaneous hypoglossal nerve activity sensing, and stimulation by eliminating stimulation artifacts that would otherwise trigger further erroneous stimulation.

12 Claims, 5 Drawing Sheets

METHOD AND APPARATUS FOR CLOSED-LOOP STIMULATION OF THE HYPOGLOSSAL NERVE IN HUMAN PATIENTS TO TREAT OBSTRUCTIVE SLEEP APNEA

CROSS-REFERENCE TO RELATED APPLICATION

This application claims the benefit of the filing date of international application no. PCT/US99/16913 having an international filing date of Jul. 27, 1999 which claims priority from U.S. provisional application No. 60/094,263 filed Jul. 27, 1998.

BACKGROUND OF THE INVENTION

The present invention relates generally to the functional electrical stimulation (FES) arts. More particularly, the present invention relates to a method and apparatus for sensing hypoglossal nerve activity in human patients to detect obstructive sleep apnea, and using the sensed hypoglossal nerve activity to trigger selective functional electrical stimulation of the hypoglossal nerve, itself, for purposes of improving upper airway patency and, thus, treating obstructive sleep apnea. Further, the present invention relates to an improved hypoglossal nerve stimulation electrode interface that allows for simultaneous hypoglossal nerve activity sensing and nerve stimulation by eliminating stimulation artifacts that would otherwise trigger further, erroneous stimulation.

Obstructive sleep apnea (OSA) is the recurrent occlusion of the upper airways of human patients during sleep. In these patients, the upper airways obstruct as often as several times a minute with each episode lasting as long as 20–30 seconds. Each apneic episode ends with a brief arousal from sleep. Consequently, arterial oxyhemoglobin saturation decreases drastically. Complications include excessive daytime sleepiness, restless sleep, morning headache, job-related accidents, impaired short-term memory, polycythema, hypertension, right-sided congestive heart failure, decreased libido, and the like. Personality disorder and other psychological problems may also develop over time. Obstructive sleep apnea is found in 2 to 4 percent of the population, primarily in adult men and post-menopausal women.

In humans, the hypoglossal nerve innervates the intrinsic and extrinsic muscles of the tongue and the geniohyoid muscle. Of these muscles innervated by the hypoglossal nerve, the genioglossus and the geniohyoid muscles are the primary muscles involved in dilating the upper airways (UAWS). Contraction of the genioglossus muscle provides tongue protrusion and, hence, dilates the airways.

It is generally known that the flow of inspired air is doubled by stimulation of the main branch of the hypoglossal nerve. Stimulation of the medial branch was nearly as effective and was superior to stimulation of other branches. Attempts have been made to improve upper airway patency in humans during sleep via direct electrical stimulation of the hypoglossal nerve. Further, various physiological variables have been used to synchronize the electrical stimulation with respiration. Hypopharyngeal or espophageal pressure measurements, airflow measurements made with thermistors placed near the nose and mouth, and tracheal inter-ring distance measurements made with a strain gauge are examples of physiological variables that have been investigated for use in synchronization of electrical stimulation of the hypoglossal nerve and/or the genioglossus muscle. However, all of these methods have drawbacks and limitations.

Other treatment methods for obstructive sleep apnea have included use of a nose mask through which continuous positive airway pressure is applied to keep the upper airways open. This therapy must be continued indefinitely, and only 60–65 percent of these patients can tolerate the technique long-term. Tracheostomy is another treatment for severe obstructive sleep apnea, but it is rarely used because of low patient acceptability and relatively high morbidity. Uvulopalatopharyngoplasty, removal of redundant tissue in the oropharynx, and other surgical operations to correct anatomical abnormalities in the upper airways can be considered in certain cases. However, in general, all of the above-mentioned therapies are associated with complications and disadvantages. Weight loss may improve the condition in mild cases, but pharmacologic attempts to treat obstructive sleep apnea by increasing pharyngeal muscle activity during sleep have not been found to be effective. Presently, electrical stimulation of the tongue muscles is the only known alternative treatment method that may provide some benefits.

In light of the foregoing, there has been found a need for a fully implantable functional electrical stimulator apparatus and method for treatment of obstructive sleep apnea that provides for both reliable detection of airway occlusion and that relieves same by selective electrical stimulation of the hypoglossal nerve. Further, a need has been identified for such a method and apparatus that accomplishes these results without relying upon use of external (i.e., non-implanted) devices that require percutaneous and/or transcutaneous interfaces and without requiring use of multiple, separate electrodes and sensors. Also, it has been deemed necessary to provide a method and apparatus for simultaneously sensing hypoglossal nerve activity and for using the sensed hypoglossal nerve activity to trigger selective electrical stimulation of the hypoglossal nerve without erroneously triggering further stimulation due to stimulation artifacts.

SUMMARY OF THE INVENTION

In accordance with the present invention, a new method and apparatus are provided for treating obstructive sleep apnea in humans by way of closed-loop electrical stimulation of the hypoglossal nerve, wherein activity of the hypoglossal nerve, itself, triggers the electrical stimulation.

In accordance with a first aspect of the present invention, a method of treating obstructive sleep apnea in a human patient comprises monitoring the patient for occlusion of his/her upper airways associated with obstructive sleep apnea by sensing electroneurogram activity of the patient's hypoglossal nerve. The hypoglossal nerve of the patient is directly electrically stimulated when occlusion of the upper airways occurs as indicated by the sensed electroneurogram activity of the hypoglossal nerve.

In accordance with a more limited aspect of the invention, the electroneurogram signal of the patient's hypoglossal nerve, itself, is used to trigger the direct electrical stimulation of the hypoglossal nerve.

In accordance with another aspect of the present invention, an apparatus for treatment of obstructive sleep apnea comprises means for detecting at least partial occlusion of upper airways of a human patient by sensing electroneurogram activity of a hypoglossal nerve of the patient. Means are provided for directly electrically stimulating the hypoglossal nerve of the patient in response to at least partial occlusion of the upper airways of the patient as indicated by the detecting means.

In accordance with still another aspect of the present invention, an apparatus adapted for simultaneously electrically stimulating body tissue and monitoring electrical activity of the body tissue being electrically stimulated without stimulation artifact is defined. The apparatus includes an electrical stimulation source and a sensor in contact with body tissue. A first stimulation contact is also in contact with the body tissue, and the said body tissue defines an electrical path between the first stimulation contact and the sensor having a first electrical impedance. A second stimulation contact is also in contact with the body tissue, and the body tissue defines an electrical path between the second stimulation contact and the sensor that has a second electrical impedance. The first impedance is substantially equal to the second impedance. A trigger receives input from the sensor and selectively triggers electrical stimulation of the body tissue by the stimulation source so that at least one electrical pulse passes between the first and second stimulation contacts through the body tissue. During stimulation, the potential difference established between the first stimulation contact and the sensor in response to the electrical pulse is substantially equal in magnitude to the potential difference established between the second stimulation contact and the sensor.

One advantage of the present invention resides in the provision of a method and apparatus for closed-loop stimulation of the hypoglossal nerve in a human to treat obstructive sleep apnea.

Another advantage of the present invention is found in the provision of a method and apparatus for treatment of obstructive sleep apnea wherein hypoglossal nerve activity is sensed and used to determine when upper airway occlusion associated with obstructive sleep apnea is occurring.

Still another advantage of the present invention is the provision of a method and apparatus for stimulation of the hypoglossal nerve in obstructive sleep apnea patients wherein sensed activity of the hypoglossal nerve in the patient triggers electrical stimulation of the hypoglossal nerve when the sensed activity of the hypoglossal nerve is indicative of occlusion of the patient's upper airways so that the occlusion is prevented or removed.

A further advantage of the present invention is the provision of a method and apparatus for closed-loop stimulation of the hypoglossal nerve in obstructive sleep apnea patients wherein hypoglossal nerve activity is sensed simultaneously with stimulation of the hypoglossal nerve.

Still another advantage of the present invention resides in the provision of an apparatus for treatment of obstructive sleep apnea in human patients wherein the apparatus is totally implantable in the patient and requires no external devices or percutaneous electrical leads.

A yet further advantage of the present invention is found in the provision of a method and apparatus for closed-loop stimulation of the hypoglossal nerve in human patients for purposes of treating obstructive sleep apnea wherein a single, multiple-contact (i.e., >1 contact) electrode is implanted in the patient for sensing/stimulation rather than multiple, separate electrodes/sensors.

A still further advantage of the present invention resides in the provision of a method and apparatus for treatment of obstructive sleep apnea wherein the onset of obstructive sleep apnea is predicted so that it can be prevented before it becomes severe.

Still other benefits and advantages of the present invention will become apparent to those of ordinary skill in the art to which the invention pertains upon reading and understanding the specification and accompanying drawings.

BRIEF DESCRIPTION OF THE DRAWINGS

The invention takes form in certain components and arrangements of components, and in certain steps and arrangements of steps, preferred embodiments of which are described herein and illustrated in the accompanying drawings that form a part hereof and wherein.

DETAILED DESCRIPTION OF THE PREFERRED EMBODIMENTS

Referring now to the drawings, wherein the showings are for purposes of describing preferred embodiments of the invention only and not for purposes of limiting same, a closed-loop method and apparatus for closed-loop stimulation of the hypoglossal nerve in human patients to treat obstructive sleep apnea is described. Heretofore, there has been insufficient understanding of the role of the hypoglossal nerve in obstructive sleep apnea and, consequently, there has not been provided a method and apparatus for treatment of obstructive sleep apnea by stimulation of the hypoglossal nerve wherein activity of the hypoglossal nerve is used to detect airway obstruction. Accordingly, FIGS. 1–4 relate to the development of the present invention through study of various dogs. Those of ordinary skill in the art will appreciate that the information set forth in FIGS. 1–4 and the accompanying text of the disclosure has application to human patients, as well.

Figure 1:
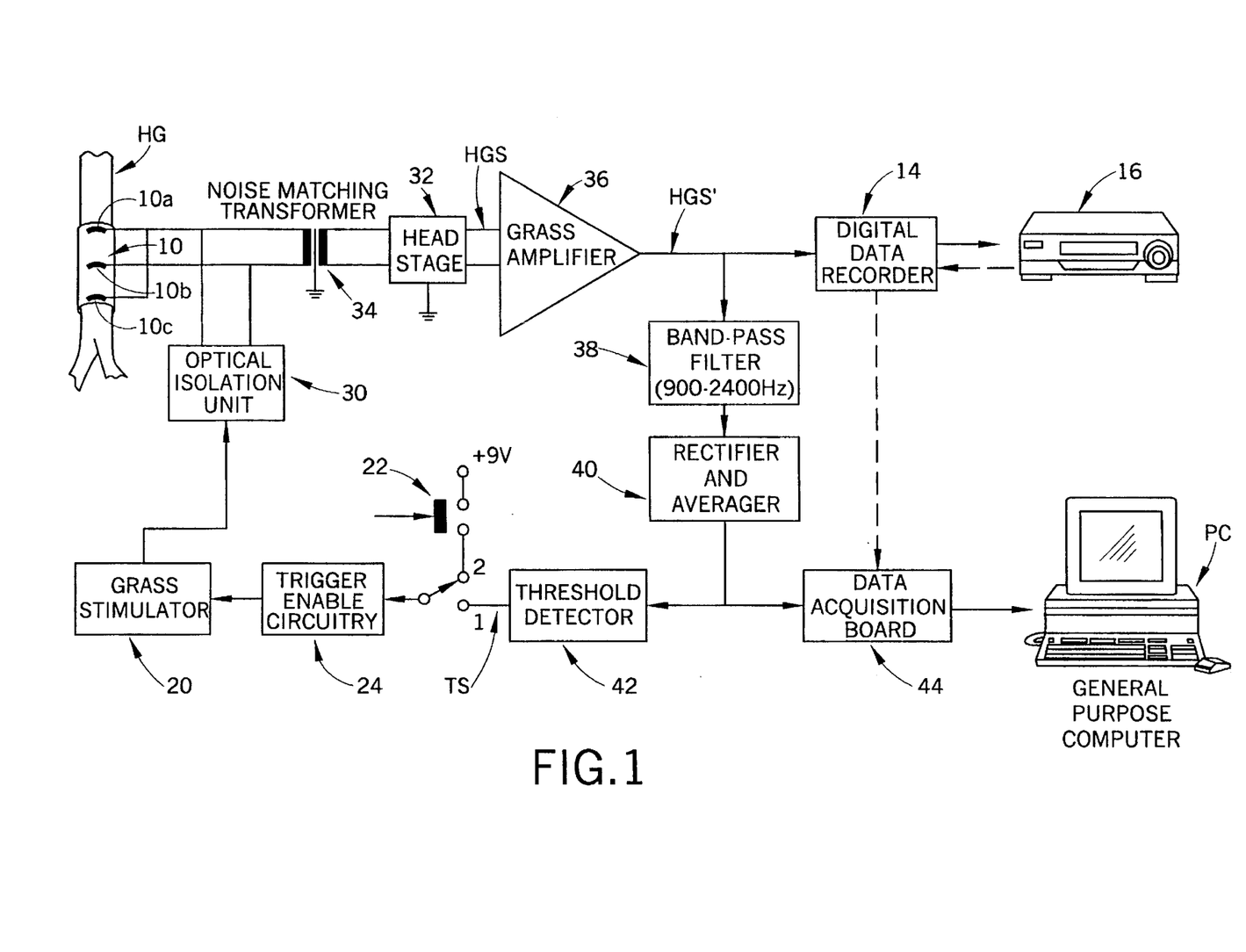
FIG. 1 is a block diagram illustrating a system used for recording hypoglossal nerve activity and for closed-loop stimulation of the hypoglossal nerve.

Referring to FIG. 1, an apparatus for studying the role of the hypoglossal nerve in obstructive sleep apnea and treatment of same is illustrated. Two healthy Beagles with normal upper airway anatomy were chronically implanted with spiral nerve cuff electrodes 10 on the main trunk of the hypoglossal nerve HG, and electroencephalogram (EEG) and electro-oculogram (EOG) electrodes (not shown) on the skull for sleep staging in the same surgical procedure. The cuff electrode 10 used for the present study were 20 millimeters (mm) in length and 2.5 mm in diameter, with first, second, and third contacts 10a,10b,10c, and were implanted bilaterally in one animal (Beagle#1) and unilaterally in the other (Beagle#2).

A custom-design apparatus that does not form part of the present invention was used to apply force selectively on the submental region of the dogs, approximately a few centimeters rostral to the hyoid bone, for purposes simulating occlusion of the upper airways in the dogs as would occur during obstructive sleep apnea in human patients. A custom-made cylindrical balloon, also not forming a part of the present invention, was placed inside the animal's esophagus before each sleep session for measurements of the esophageal pressure (Pes) Respiratory abdominal movements ABD (FIG. 2) of each dogs were measured with a plethysmograph that had an inductive band transducer worn around the belly. All the raw signals were continuously digitized by a digital data recorder 14, such as a Digital Data Recorder Model VR-10B available commercially from Instrutech Corp., New York. The raw data signals were also and stored on video tapes by a video tape recorder 16 during sleep sessions.

With the two dogs studied, a total of 53 sleep sessions were held spread over a period of 17 months. Each session lasted between 2–4 hours and included multiple sleep cycles. Non-Rapid Eye Movement (NREM) sleep stage was characterized with larger amplitudes and slower frequency components in the EEG signal relative to either wakefulness or Rapid Eye Movement (REM) sleep stage. The maximum submental force applied using the force applicator was defined as the largest force value at which the animal was not aroused from sleep.

Hypoglossal nerve HG stimulation was by a conventional pulse train stimulator 20, such as a Grass S88 stimulator available commercially from Grass Medical Instruments, at the maximum submental force level in some of the sessions using either manual triggering via switch 22 in the beginning of each breath or in a closed-loop manner using activity of the hypoglossal nerve HG, itself, as the trigger with the switch 22 in position "1." Here, at this early stage of the study, false triggers due to stimulation artifacts in the electroneurogram signal of the hypoglossal nerve HG as recorded by the recorder 14 were prevented by disabling the output of the trigger enabling circuit 24 for about an interbreath interval.

Electrical stimulation from the stimulator 20 was applied to the hypoglossal nerve HG between the second (middle) contact lob and the first and third (end) contacts 10a,10c of the tripolar cuff electrode 10 through an optically isolated voltage to current converter unit 30. A train of cathodic pulses with a train duration of 1–3 seconds at a pulse frequency of approximately 40 Hz, pulse width of 100 microseconds ($\mu$S) and at pulse amplitudes between 0.2 to 0.6 milliamps (mA) were used. Ten breaths during and ten breaths between the stimulated breaths were allowed before raising the current amplitude to a higher value.

The hypoglossal nerve electroneurogram signal HGS was amplified and filtered between 300 Hertz (Hz) and 10 Kilohertz (kHz) by amplifier 36 such as a P5 Series amplifier also available commercially from Grass Medical Instruments resulting in the signal HGS'. The electroencephalogram and EOG signals (not shown) were band-pass filtered between 1 Hz to 30 Hz. The pressure measurements from the submental force applicator and the esophageal balloon were amplified with custom-made DC amplifiers (not shown). The amplified signal HGS' from the hypoglossal nerve HG was digitized and converted to an appropriate format for storing on video tapes at a rate of 47.2 kilosamples/second by the digital data recorder 14. Other raw signals were digitized at a rate of 60 sample/s.

The recordings of the amplified hypoglossal nerve signal HGS' were further filtered with a custom design band-pass filter 38. The band-pass filter 38 comprised a third order high pass Butterworth filter at 900 Hz and a second order low pass Butterworth filter at 2400 Hz to eliminate electromyogram (EMG) contamination from the nearby muscles and passed through a rectifier and 100 millisecond (ms) time averager 40, and a threshold detector 42 to produce the trigger signal TS for electrical stimulation of the hypoglossal nerve HG via stimulator 20.

For frequency spectrum analysis, the raw hypoglossal nerve signals HGS' were replayed from the video tapes and resampled at a rate of 20,000 samples/second using a data acquisition board 44 and a programmed general purpose computer PC. For breath-by-breath analysis and the temporal plots of the data, the rectified and averaged version of the hypoglossal nerve signal HGS' and other measured variables were sampled at a rate of 60 sample/second into the computer PC. The area under the esophageal pressure trace during the inspiratory time (AreaPes) was calculated in each breath to evaluate the effect of loading and electrical stimulation on the size of the upper airway passage.

Figure 2:
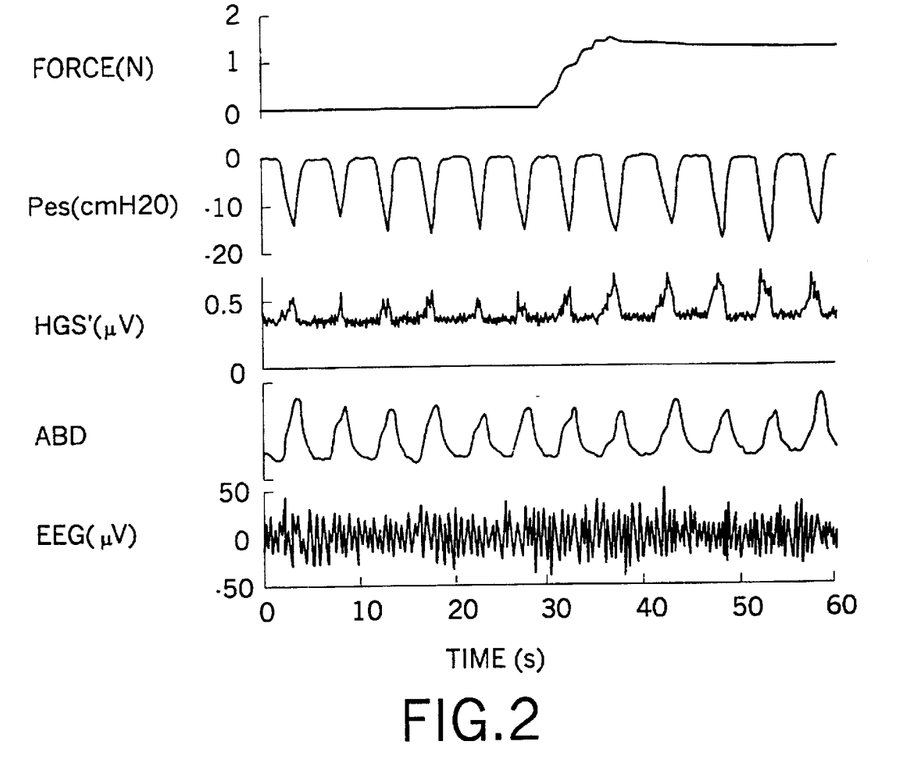
FIG. 2 graphically illustrates hypoglossal nerve response when airway occlusion was caused by application of force.

Recordings of the hypoglossal nerve signal HGS' had a phasic component above a baseline when the upper airways in the dogs were loaded with the submental force in NREM sleep to cause occlusion of the airways. The phasic activity of the hypoglossal nerve signal HGS' increased immediately in the following breath as a response to an increase in the submental force and stayed at an elevated activity level as long as the force was applied as illustrated in FIG. 2.

The mean signal-to-noise ratio in the hypoglossal nerve signal HGS', defined as the peak phasic activity divided by the baseline in signal after it has been rectified and averaged by the rectifier/averager 40, had a mean±standard deviation of 2.37±0.74 (n=25 force maneuvers) at the maximum submental force level. The hypoglossal nerve HG was active in every breath cycle at the maximum submental force level. Airflow-limited inspiration was often observed at the maximum force as confirmed by the presence of snoring. The esophageal pressure Pes also increased with application of the submental force. The correlation between the area of phasic hypoglossal nerve HG activity and AreaPes, was R=0.82 and R=0.88 for the two dogs, respectively. The onset time of the phasic hypoglossal nerve HG activity with respect to the beginning of the phasic esophageal pressure was measured at the maximum force level on breath-by-breath basis in multiple trials. The phasic hypoglossal nerve signal HGS' began to rise earlier than the esophageal pressure with a mean+standard deviation onset time of 17±196 ms (220 breaths in 20 force maneuvers).

Figure 3:
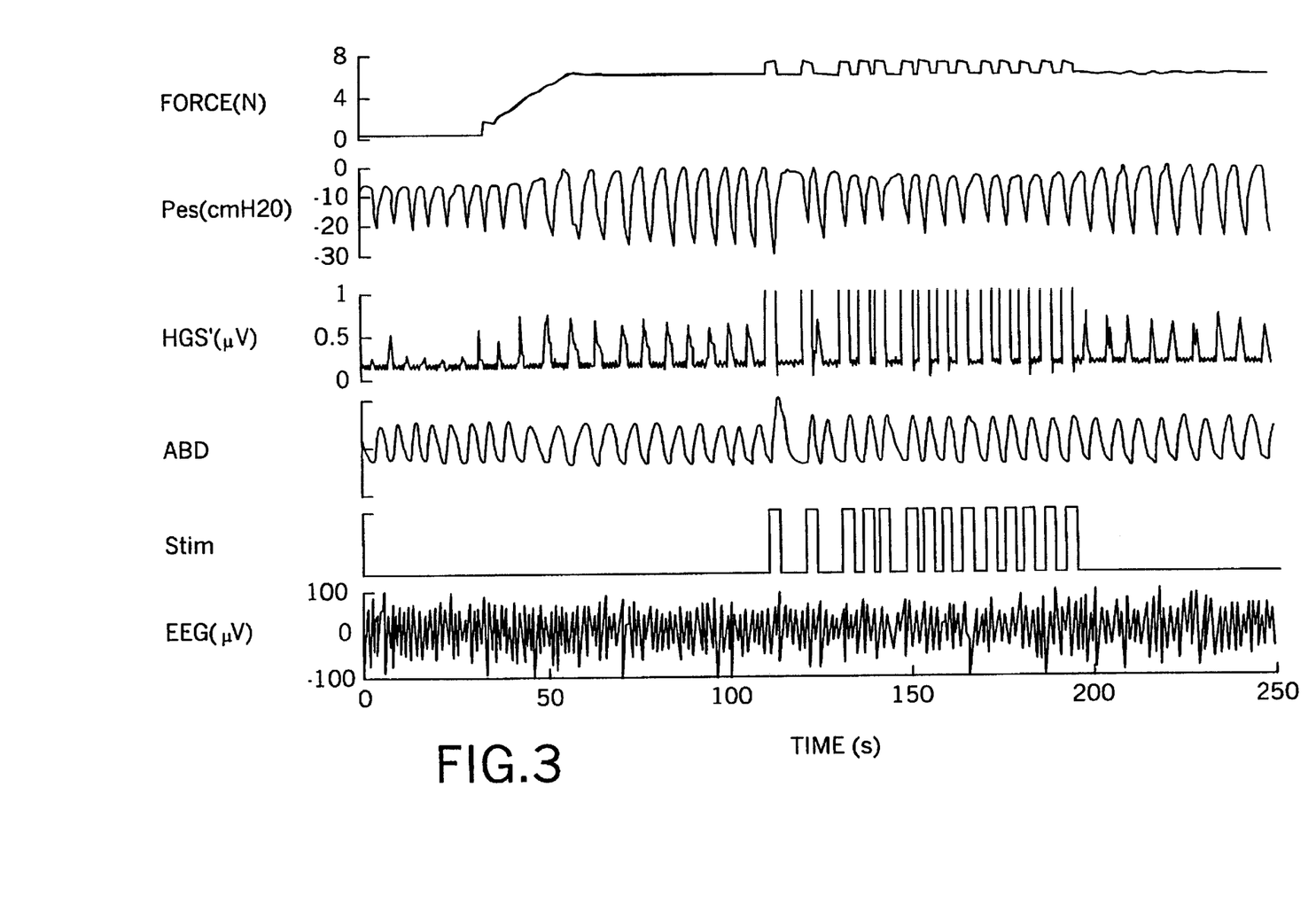
FIG. 3 graphically illustrates closed-loop stimulation of the hypoglossal nerve during NREM sleep using electroneurogram activity of the hypoglossal nerve, itself, to trigger the electrical stimulation.

FIG. 3 demonstrates closed-loop stimulation of the hypoglossal nerve using its own electroneurogram activity as the feedback signal. The submental force to cause airway occlusion was first raised to 6 N to load the upper airways. As a result, the phasic components of the submental force and the hypoglossal nerve activity signal HGS' increased. The closed-loop operation was started at time=110 seconds. In this (and all other) stimulation trial(s), the threshold for triggering stimulation of the hypoglossal nerve in the activity signal HGS was set just above the baseline of same. At the start of each breath, the electronic circuitry detected the onset of the phasic hypoglossal nerve activity signal HGS' and triggered the stimulator 20 that, in turn, generated a train of pulses (pulse width=100 $\mu$s at 40 Hz) for a predetermined period of time (3s). Upon detection of each phasic component of the activity signal HGS', the output of the trigger enable circuit 24 was disabled for approximately one interbreath interval (5 s) to prevent false stimulation of the nerve due to the stimulation artifacts in the nerve activity signal HGS'. Using the system of FIG. 1, the phasic bursts of the activity signal HGS' were completely obscured by the stimulation artifacts in the recordings since the detection occurred very early in each breath cycle. The animal took a deeper breath on the first stimulated breath indicating a relief from the effect of the submental force. The amplitude of the phasic esophageal pressure (Pes) stayed at a low level as long as the electrical stimulation (Stim) was applied and returned to its pre-stimulation level within the next breath at the end of the stimulation. The EEG channel indicated no arousal from sleep during stimulation.

Figure 4:
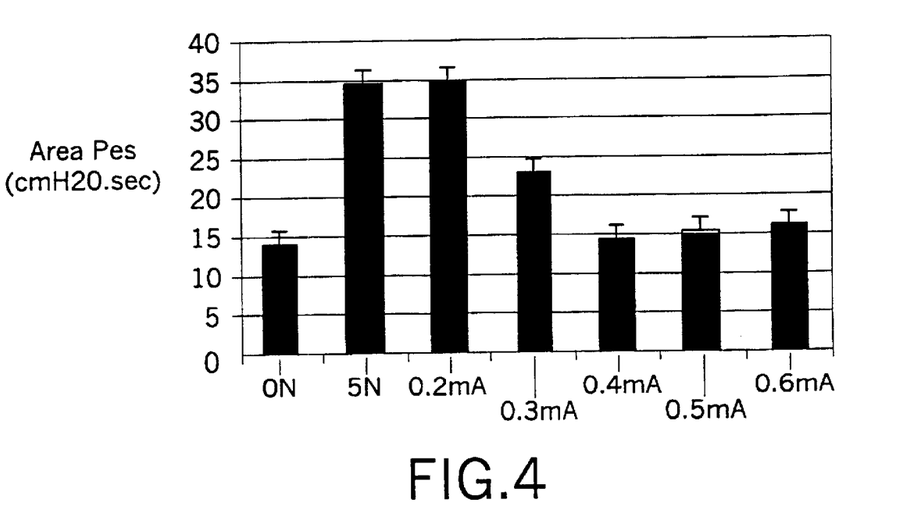
FIG. 4 graphically illustrates esophageal pressure under normal conditions, airway occlusion, and hypoglossal nerve electrical stimulation during airway occlusion.

The effect of the electrical stimulation on the area of the phasic esophageal pressure (AreaPes) in NREM sleep is shown in FIG. 4. The submental force value of 0 Newtons (N), representing no airway occlusion, was applied as control. A submental force application value of 5 N caused airway occlusion and a 2 to 3 fold increase in AreaPes. Direct electrical stimulation of the hypoglossal nerve HG at 0.2 mA did not result in significant large changes in the pressure measurements. However, AreaPes fell rather sharply with increasing current amplitudes of the stimulus pulse train (Stim) and it returned to near control values indicating a complete removal of the upper airway occlusion effect caused by the submental force application. In these trials, the animal was not aroused from sleep even at a current amplitudes 50% larger than what was sufficient to completely reverse the loading effect of the submental force (0.6 mA vs. 0.4 mA).

The foregoing shows the feasibility of the closed-loop stimulation of the hypoglossal nerve HG using it's activity HGS,HGS' as the feedback signal. The hypoglossal nerve signal recordings obtained with cuff electrodes 10 have sufficiently large signal-to-noise ratios for detection of the phasic component without missing a breath when the airways are loaded with the maximum force. Conventional filtering techniques and algorithms are adequate to prevent false detections due to baseline shifts and electromyogram (EMG) contamination from the surrounding muscles. The hypoglossal nerve signal HGS' recorded in this study is thought to be primarily of efferent origin since the afferent fibers in the hypoglossal nerve HG are few in number.

Figure 5:
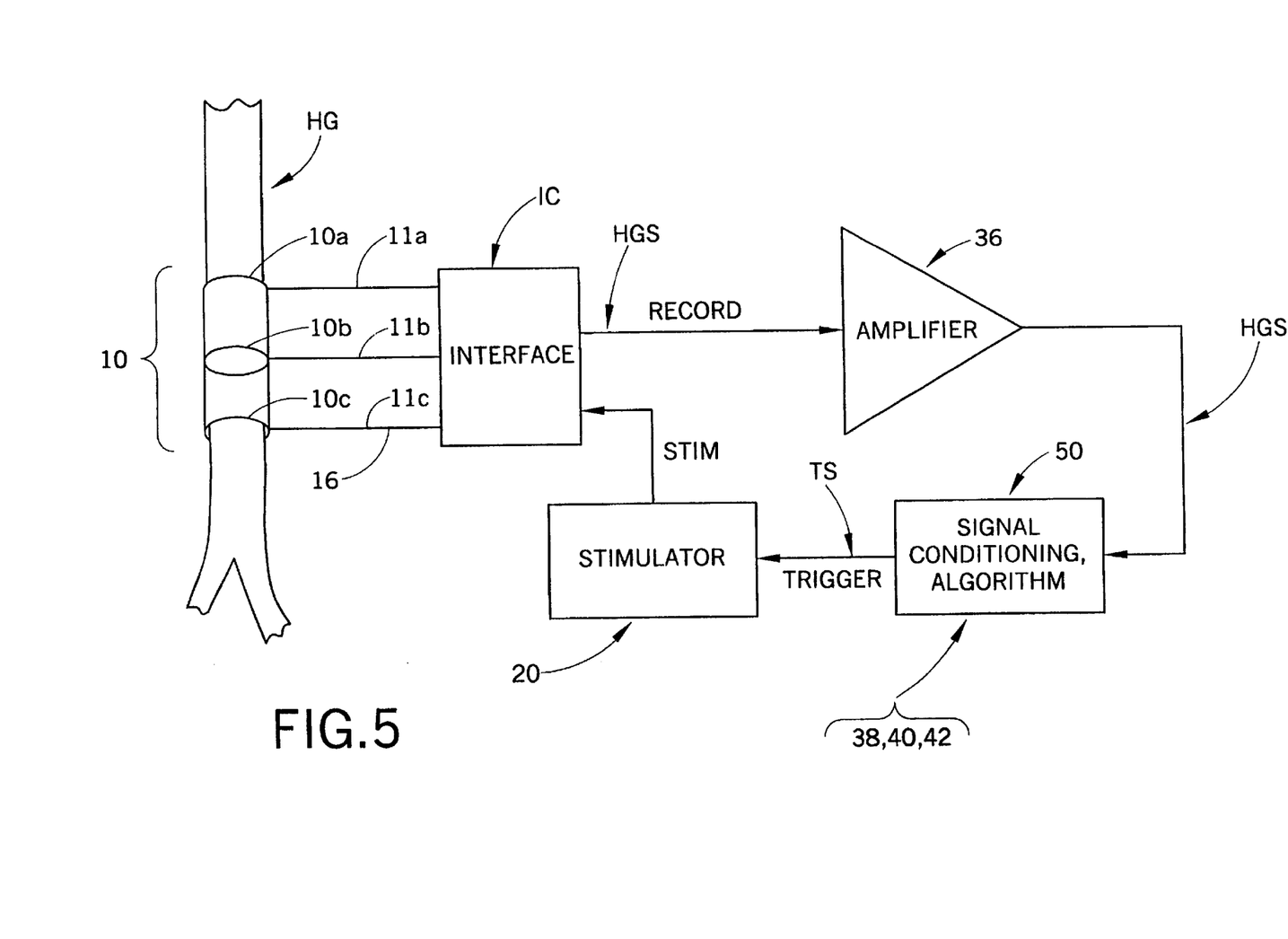
FIG. 5 is a diagrammatic illustration of a closed-loop system for stimulation of the hypoglossal nerve for treatment of obstructive sleep apnea in accordance with a preferred embodiment of the present invention; and, FIG. 6 is a schematic diagram of an electrode/sensor interface circuit formed in accordance with the present invention and adapted for closed-loop stimulation of the hypoglossal nerve of a human patient for treatment of obstructive sleep apnea wherein stimulation artifacts are eliminated from the sensing circuit to prevent erroneous stimulation in response to the artifacts.

FIG. 5 diagrammatically illustrates a preferred embodiment of an apparatus for closed-loop stimulation of the hypoglossal nerve HG in human patients to treat obstructive sleep apnea. The apparatus illustrated in FIG. 5 is similar to that illustrated in FIG. 1 and is adapted for connection to the tri-polar nerve cuff electrode 10 including first, second, and third contacts 10a,10b,10c adapted for connection about the hypoglossal nerve HG of the patient being treated and connected to an electrode interface circuit IC via first, second, and third leads 11a,11b,11c, respectively. The electrode 10 acts as both hypoglossal nerve stimulation electrode and a hypoglossal nerve activity sensor as described in full detail below. The apparatus illustrated in FIG. 5 is adapted for total implantation in the patient being treated without the need for associated external components. Those of ordinary skill in the art will recognize that electrodes other than the illustrated tri-polar electrode may be used without departing from the overall scope and intent of the present invention. It is not intended that the invention be limited to any particular type of electrode.

The interface circuit IC receives hypoglossal nerve electroneurogram activity input from the electrode 10 and supplies a hypoglossal nerve activity signal HGS to the amplifier 36. The amplifier 36, described in detail above in relation to FIG. 1, supplies an amplified and filtered hypoglossal nerve activity signal HGS' to a signal conditioning and algorithm circuit 50 that comprises the band-pass filter 38, the rectifier and averager 40, and the threshold detector 42 described above. When the threshold detector 42 of the signal conditioning and algorithm circuit 50 detects at least partial occlusion of the patient's upper airways by corresponding hypoglossal nerve activity above a select threshold as indicated by the amplified/filtered signal HGS', it outputs a trigger signal TS to the stimulator 20. When the stimulator 20 receives the trigger signal TS, it outputs a stimulation pulse train (Stim) to the hypoglossal nerve HG by way of the interface circuit IC and electrode 10 to lessen the airway occlusion and prevent obstructive sleep apnea. Preferably, in the closed-loop system, the stimulator 20 is triggered to output the stimulation pulse train (Stim) whenever electroneurogram activity of the hypoglossal nerve HG is above a select threshold over the baseline, i.e., when electroneurogram activity of the hypoglossal nerve HG exceeds the baseline activity experienced when no occlusion of the upper airways is present by a select amount. Of course, the baseline activity for a particular patient cannot be determined until the closed-loop stimulation apparatus is implanted and tested.

Figure 6:
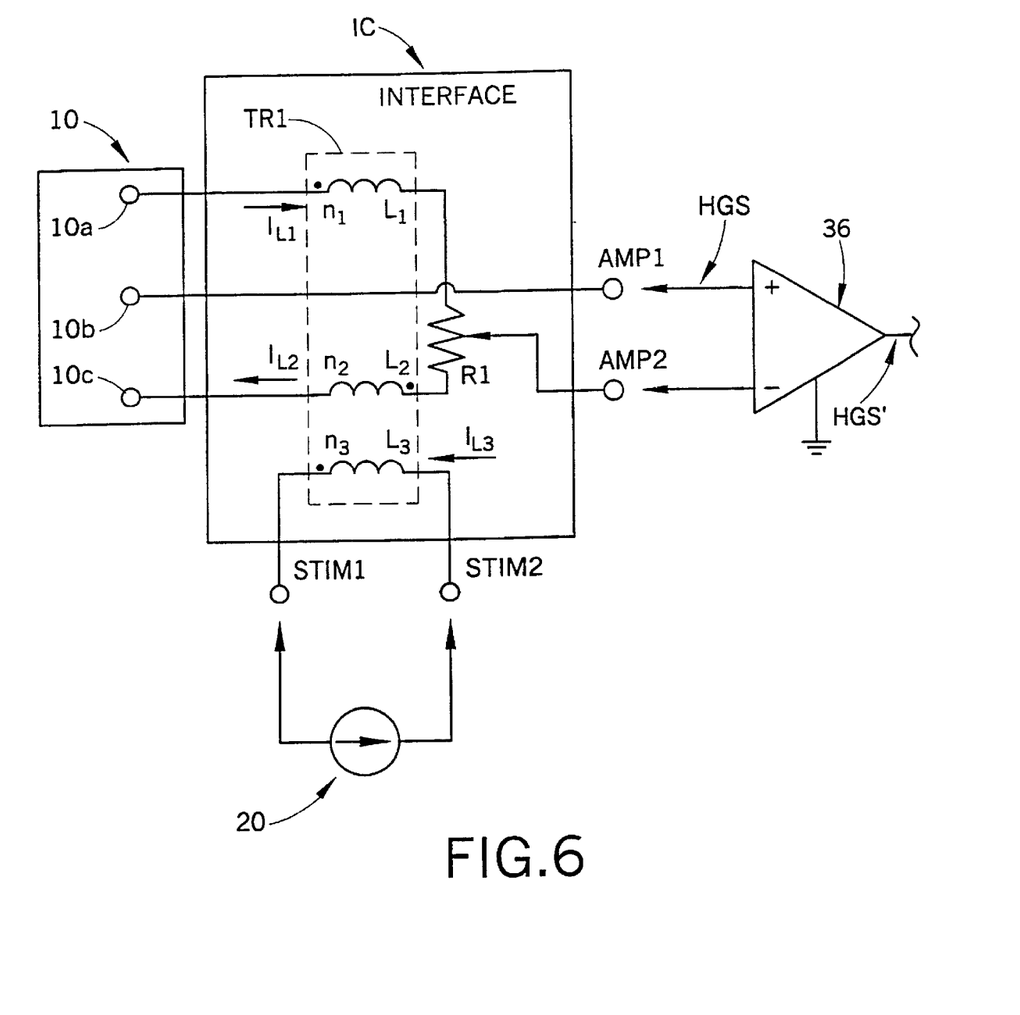

Operation of the interface circuit IC is best understood with reference also to FIG. 6. In general, the electrode is connected to the interface circuit IC so that the first and third electrode contacts 10a,10c act as stimulation contacts and so that the central, second contact 10b acts as a hypoglossal nerve electroneurogram activity sensor. The interface circuit IC has been found to be highly desirable because, as described herein, it suppresses electromyogram (EMG) signals from muscles surrounding the hypoglossal nerve HG to prevent these signals from interfering with accurate sensing of hypoglossal nerve activity. Further, the interface circuit IC suppresses stimulation artifacts in the hypoglossal nerve activity signal HGS due to application of the stimulation pulse train (Stim) by the stimulator 20.

More particularly, as illustrated in FIG. 8, the interface circuit IC comprises a transformer TR1 including first, second, and third inductor coils L1,L2,L3, and further comprises a variable resistor such as the potentiometer R1. The amplifier 36 is connected to first and second output terminals AMP1,AMP2. The stimulator 20 is connected to the interface circuit IC by way of first and second input terminals STIM1,STIM2 so as to be connected across the coil L3 of the transformer TR1. The transformer TR1 is designed to operate at the frequency of the stimulation pulse train input signal (Stim), and the coils L1,L2,L3 of the transformer are very tightly coupled to minimize stray inductances. The reactive impedances of the "magnetizing coils" are also very high in the input signal (Stim) operating frequency range. Those of ordinary skill in the art will recognize that the transformer TR1 need not be large because the energy transferred thereby is only severalmilliwatts.

In operation, when the stimulation input signal (Stim) is input to the interface circuit IC, the voltage induced across the coil L3 by the current IL3 is also induced across the coils L1,L2 of a like amplitude (n1=n2) by the currents IL1,IL2. This, then causes stimulation of the hypoglossal nerve HG by a current IL1,IL2 that flows through a circuit comprising the coils L1,L2, the third contact 10c, the tissue of the hypoglossal nerve HG, and the first electrode contact 10a. The stimulation artifact is canceled from the hypoglossal nerve activity signal HGS due to the fact that the sensing contact 10b divides the impedance between the first and third contacts 10a,10c equally. Thus, the bridge consisting of the tissue of the hypoglossal nerve HG and the transformer TR1 is balanced so that, upon stimulation of the nerve HG, no potential difference is present at the first and second output terminals AMP1,AMP2 connected to the amplifier 36. On the other hand, pure hypoglossal nerve electroneurogram activity, itself, will cause a potential difference at the terminals AMP1,AMP2 and cause amplification of the signal HGS that is then fed to the signal conditioning and algorithm circuit 50 as described above. If necessary, the potentiometer R1 can be adjusted after the device is implanted to ensure that the bridge is balanced and the stimulation artifact canceled. Furthermore, undesirable electromyogram (EMG) activity received through the first and third contacts 10*a*,10*c* is also canceled out due to the symmetrical arrangement of the contacts 10*a*,10*c* and the coils L1,L2.

In light of the foregoing, those of ordinary skill in the art will recognize that the present invention provides a method and apparatus for using electroneurogram activity of the hypoglossal nerve to detect occlusion of the upper airways in a human patient, and for using the electroneurogram signal sensed from the hypoglossal nerve to trigger direct electrical stimulation of the hypoglossal nerve to remove the airway occlusion.

The invention has been described with reference to preferred embodiments. Obviously, modifications and alterations will occur to others upon reading and understanding the preceding specification. It is intended that the invention be construed as including all such modifications and alterations insofar as they are within the scope of the appended claims and equivalents thereto.

Having described the preferred embodiments, the invention is claimed to be:

1. A method of treating obstructive sleep apnea in a human patient, said method comprising:

monitoring said human patient for at least partial occlusion of upper airways of said patient associated with obstructive sleep apnea by sensing electroneurogram activity of a hypoglossal nerve of the patient; and, directly electrically stimulating the hypoglossal nerve of the patient when at least partial occlusion of the upper airways of the patient occurs as indicated by said sensed electroneurogram activity of said hypoglossal nerve.

2. The method of treating obstructive sleep apnea as set forth in claim 1 wherein said step of monitoring said human patient for occlusion of the upper airways comprises:

identifying at least partial occlusion of the upper airways of the patient when said sensed hypoglossal nerve electroneurogram activity rises above a baseline electroneurogram activity level of said hypoglossal nerve by a select amount, said baseline electroneurogram level corresponding to a level of electroneurogram activity of said hypoglossal nerve present when said upper airways of said patient are not at least partially occluded.

3. The method of treating obstructive sleep apnea as set forth in claim 1 further comprising:

amplifying said sensed electroneurogram activity of said hypoglossal nerve to obtain an amplified electroneurogram signal; and, using said amplified electroneurogram signal to trigger said direct electrical stimulation of said hypoglossal nerve.

4. The method of treating obstructive sleep apnea as set forth in claim 1 wherein stimulating the hypoglossal nerve of the patient is accomplished with a train of stimulus pulses each having an amplitude of greater than 0.2 mA.

5. The method of treating obstructive sleep apnea as set forth in claim 1 wherein said step of directly electrically stimulating said hypoglossal nerve comprises:

connecting a nerve electrode to said hypoglossal nerve so that said nerve electrode at least partially encircles said hypoglossal nerve; and passing electrical stimulation pulses between first and second contacts of said nerve electrode through tissue of said hypoglossal nerve.

6. The method of treating obstructive sleep apnea as set forth in claim 5 wherein said step of monitoring said human patient for at least partial occlusion of the upper airways by sensing electroneurogram activity of said hypoglossal nerve comprises:

sensing electroneurogram activity of said hypoglossal nerve with a third contact of said nerve electrode, said third contact arranged relative to said first and second contacts so that a first impedance defined between said first contact and said third contact through said tissue of said hypoglossal nerve is substantially equal to a second impedance defined between said second contact and said third contact through said tissue of said hypoglossal nerve.

7. An apparatus for treatment of obstructive sleep apnea in a human patient, said apparatus comprising:

means for detecting at least partial occlusion of upper airways of said human patient by sensing electroneurogram activity of a hypoglossal nerve of the patient; and, means for directly electrically stimulating the hypoglossal nerve of the patient in response to at least partial occlusion of the upper airways of the patient as indicated by said means for detecting at least partial airway occlusion.

8. The apparatus for treatment of obstructive sleep apnea as set forth in claim 7 wherein said means for detecting at least partial airway occlusion detects at least partial occlusion of the upper airways of the patient when said sensed hypoglossal nerve electroneurogram activity rises above a baseline electroneurogram activity level of said hypoglossal nerve by a select amount, said baseline electroneurogram level corresponding to a level of electroneurogram activity of said hypoglossal nerve present when said upper airways of said patient are not at least partially occluded.

9. The apparatus as set forth in claim 7 further comprising:

means for amplifying said sensed electroneurogram activity of said hypoglossal nerve to obtain an amplified electroneurogram signal; and, trigger means for receiving said amplified electroneurogram signal and triggering said direct electrical stimulation of said hypoglossal nerve when said amplified signal exceeds a baseline activity level of said signal by a select amount.

10. The apparatus as set forth in claim 7, wherein said means for electrically stimulating the ypoglossal nerve of the patient stimulates the hypoglossal nerve with a train of stimulus pulses each having an amplitude of greater than 0.2 mA.

11. The apparatus as set forth in claim 7 further comprising:

a nerve electrode having two contacts, said electrode adapted to be connected to and at least partially encircling said hypoglossal nerve, wherein said means for electrically stimulating said hypoglossal nerve passes electrical stimulation pulses between said first and second contacts of said nerve electrode through tissue of said hypoglossal nerve.

12. The apparatus as set forth in claim 11 further comprising a third contact on said electrode, wherein said means for detecting at least partial occlusion of said patient's airways senses electroneurogram activity of said hypoglossal nerve with said third contact of said nerve electrode, said third contact arranged relative to said first and second contacts so that a first impedance defined between said first contact and said third contact through said tissue of said hypoglossal nerve is substantially equal to a second impedance defined between said second contact and said third contact through said tissue of said hypoglossal nerve.

* * * * *